US012673065B2

(12) United States Patent
El-Hashim et al.

(10) Patent No.: US 12,673,065 B2
(45) Date of Patent: Jul. 7, 2026

(54) ANTI-INFLAMMATORY COMPOSITION AND METHOD OF TREATMENT

(71) Applicant: KUWAIT UNIVERSITY, Safat (KW)

(72) Inventors: Ahmed El-Hashim, Safat (KW); Khaled Orabi, Safat (KW); Maitham Abbas Khajah, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 0 days.

(21) Appl. No.: 17/325,925

(22) Filed: May 20, 2021

(65) Prior Publication Data

US 2022/0062298 A1 Mar. 3, 2022

Related U.S. Application Data

(60) Provisional application No. 63/073,877, filed on Sep. 2, 2020.

(51) Int. Cl.
| | |
|---|---|
| *A61K 31/573* | (2006.01) |
| *A61K 36/8962* | (2006.01) |
| *A61P 11/06* | (2006.01) |
| *A61P 29/00* | (2006.01) |

(52) U.S. Cl.
CPC ........ *A61K 31/573* (2013.01); *A61K 36/8962* (2013.01); *A61P 11/06* (2018.01); *A61P 29/00* (2018.01)

(58) Field of Classification Search
CPC .............. A61K 2300/00; A61K 31/573; A61K 36/8962; A61P 11/06; A61P 29/00
See application file for complete search history.

(56) References Cited

U.S. PATENT DOCUMENTS

| | | |
|---|---|---|
| 2007/0231409 A1 | 10/2007 | Huber |
| 2008/0300226 A1 | 12/2008 | Goede |
| 2018/0169019 A1* | 6/2018 | Muenster ................ A61P 35/00 |

FOREIGN PATENT DOCUMENTS

| | | |
|---|---|---|
| KR | 20040079310 A | 9/2004 |
| KR | 20090092480 A | 9/2009 |
| RU | 2253472 C1 | 6/2005 |

OTHER PUBLICATIONS

Dawud, Bayero Journal of Pure and Applied Sciences, 9(2): 95-101, Jun. 2016 (Year: 2016).*
Polukonova et al (Russian Open Medical Journal 2014; 3: 0304) (Year: 2014).*
Beasley, R., et al., "Inhaled Corticosteroid Therapy in Adult Asthma", Am J Respir Crit Care Med, 199(12): pp. 1471-1477, 2019.
Ghorani, V., et al., "The Effects of Allium Cepa Extract on Tracheal Responsiveness, Lung Inflammatory Cells and Phospholipase A2 Level in Asthmatic Rats", Iran J Allergy Asthma Immunol, 17(3): pp. 221-231, 2018.
Oliveira, T. T., et al., "Potential therapeutic effect of Allium cepa L. and quecetin in a murine model of Biomia tropicalis induced asthma", Daru J Pharmaceutical Sciences, 23(18): 12 pp., 2015.

* cited by examiner

*Primary Examiner* — Jean P Cornet
(74) *Attorney, Agent, or Firm* — Nath, Goldberg & Meyer; Joshua B. Goldberg

(57) ABSTRACT

The anti-inflammatory composition may be administered to a subject in need thereof to prevent or reduce inflammation, including inflammation resulting from asthma. The anti-inflammatory composition may comprise both onion bulb extract and one or more glucocorticosteroids, particularly a low-dose glucocorticosteroid. The anti-inflammatory composition may be administered to a subject at risk of developing asthma to prevent the progression of asthma. The anti-inflammatory composition may act by reducing pEGFR levels, or by inhibiting other inflammatory pathways.

4 Claims, 4 Drawing Sheets

ANTI-INFLAMMATORY COMPOSITION AND METHOD OF TREATMENT

CROSS-REFERENCE TO RELATED APPLICATION

This application claims the benefit of U.S. Provisional Patent Application No. 63/073,877, filed on Sep. 2, 2020.

BACKGROUND

1. Field

The disclosure of the present patent application relates to natural product extracts having medicinal value, and particularly to an anti-inflammatory composition and method of treatment.

2. Description of the Related Art

Natural products have been the cornerstone of therapeutic agents for millennia, and more recently, an important source of therapeutic drugs with unique structural diversity and pharmacological actions. Many therapeutic agents currently in use in several therapeutic areas, such as cardiovascular, oncology, and transplantation, are natural products or their derivatives, such as digoxin, vincristine and cyclosporine, respectively. However, their use as pharmaceutical agents has waned over the last few decades in the face of advances in combinatorial chemistry and biopharmaceutical technology; the latter supplying the majority of the top ten block buster drugs in the market in 2018. Indeed, more than 70% of the world's population use herb-based medicines for primary healthcare. A study in the UK has also reported that approximately 60% of asthma patients in the UK have used herbal remedies for their asthma. These findings suggest a strongly held belief that natural products have therapeutic benefit in a wide range conditions and are also safe.

Inflammatory-based diseases, such as asthma, present a global healthcare challenge. Worldwide prevalence of asthma has been estimated to range from 1% to as high as 18% in different populations, affecting up to 300 million people worldwide with increasing prevalence particularly among children. It is currently the most common chronic respiratory disease in children and costs over a £1 billion per year in some healthcare systems in Europe. There is also good evidence that food allergy and eczema are rising in parallel to asthma and have been described as a "second wave" of an allergy epidemic, particularly in children. While the mechanisms of asthma still remain unclear, it is well recognized that chronic airway inflammatory disease is central to its pathogenesis and is mediated by inflammatory cells, such as mast cells and eosinophils, and is driven by specific Th2 and Th17 lymphocytes, cytokines and chemokines.

There have been several recent studies demonstrating that pathogenic EGF/EGFR-dependent signaling through EGF (epidermal growth factor) and other EGFR (epidermal growth factor receptor) ligands, such as amphiregulinin, is increased in asthma. EGFR expression has been reported to be weak or absent in healthy individuals, but is significantly increased in the airway epithelium of not only asthmatics, but also in patients with COPD (chronic obstructive pulmonary disease), and cystic fibrosis (CF) patients. Furthermore, in a recent clinical study conducted using ex vivo lung tissue from patients with COPD, the EGFR inhibitor BIBW 2948 showed some efficacy in inhibiting EGFR phosphorylation and a tendency toward reducing mucous cell metaplasia. More importantly, a positive correlation between EGFR immunoreactivity and MUC5AC mucin staining was noted when bronchial biopsies from healthy volunteers and subjects with mild-to-moderate asthma were compared, suggesting a causal relationship. Also, areas of epithelial damage in asthmatic patients exhibited a strong EGFR immunoreactivity, suggesting that EGFR activation plays an important role in the epithelial damage/repair process in asthma. Of interest also is that a positive correlation between mucin and EGFR staining has been shown in the small airway of CF patients. Thus, increased EGFR expression is a consistent finding not only is asthma, but across several disease states. Moreover, pre-clinical animal models have also demonstrated a strong role for EGFR in asthma. We (and others) have shown, using an allergic model of inflammation, that EGFR inhibitors, such as AG1478 or gefitnib, significantly reduces eosinophil recruitment, airway inflammation, airway hyperresponsiveness (AHR), and goblet cell hyper/metaplasia, thus underscoring the importance of this signaling pathway in asthma pathogenesis. Furthermore, we have also reported that ERK1/2 and AKT are downstream signaling molecules of EGFR activation. Therefore, both clinical and preclinical studies clearly establish an important role for EGFR-dependent signaling in inflammatory-based diseases.

While the combination of inhaled corticosteroids (ICS) and long-acting beta-agonists (LABA) is a main treatment advocated by most asthma guidelines, a significant number of patients are poorly compliant with inhaled treatments and remain under-controlled. Furthermore, severe asthmatics require treatment with moderate to high doses of steroids. This is associated with a significant side-effect profile. Therefore, it would be more advantageous if the asthma therapeutic goals can be achieved at lower doses of steroids, since the side effects would be minimal.

Moreover, novel monoclonal antibody-based therapy in inflammatory disease management has made an impact on disease control. For example, the anti-IgE antibody omalizuma has been used as a steroid-sparing drug in patients with severe asthma, but unfortunately its use is limited due to a high frequency of anaphylactic reaction and serum sickness, and lack of cost-effectiveness. Similarly, the use of the newly introduced anti-IL5 antibodies, such as mepolizumab and benralizumab, is limited to severe asthmatics with a high eosinophilic component. However, concerns have been raised regarding their cost-effectiveness. Despite the recent market increase in therapeutic agents that selectively target specific molecules, it is unlikely that the blockade of individual mediator signaling pathways would result in optimal therapeutic outcomes in asthma, and monoclonal based therapy would certainly be beyond the financial reach of most asthma patients in the developing world due to their high cost.

Thus, an anti-inflammatory composition and method of treatment solving the aforementioned problems are desired.

SUMMARY

The anti-inflammatory composition may be administered to a subject in need thereof to prevent or reduce inflammation, including inflammation resulting from asthma. The anti-inflammatory composition may comprise both onion bulb extract and one or more glucocorticosteroids, or both onion bulb extract and a low-dose glucocorticosteroid. The anti-inflammatory composition may be administered to a subject at risk of developing asthma to prevent the progression of asthma. The anti-inflammatory composition may act by reducing pEGFR levels, or by inhibiting other inflammatory pathways.

The anti-inflammatory composition may include a pharmaceutically acceptable carrier.

The anti-inflammatory composition may include onion bulb extract, a glucocorticosteroid, and a pharmaceutically acceptable carrier.

A method of making the anti-inflammatory composition may include mixing the anti-inflammatory composition under sterile conditions with a pharmaceutically acceptable carrier and preservatives, buffers, or propellants to create a pharmaceutical composition, and providing the pharmaceutical composition in a form suitable for daily, weekly, or monthly administration.

A method of treating an inflammatory disease may include administering to a subject in need thereof a therapeutically effective amount of the pharmaceutical composition described above A method of treating asthma may include administering to a subject in need thereof a therapeutically effective amount of the pharmaceutical composition described above.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
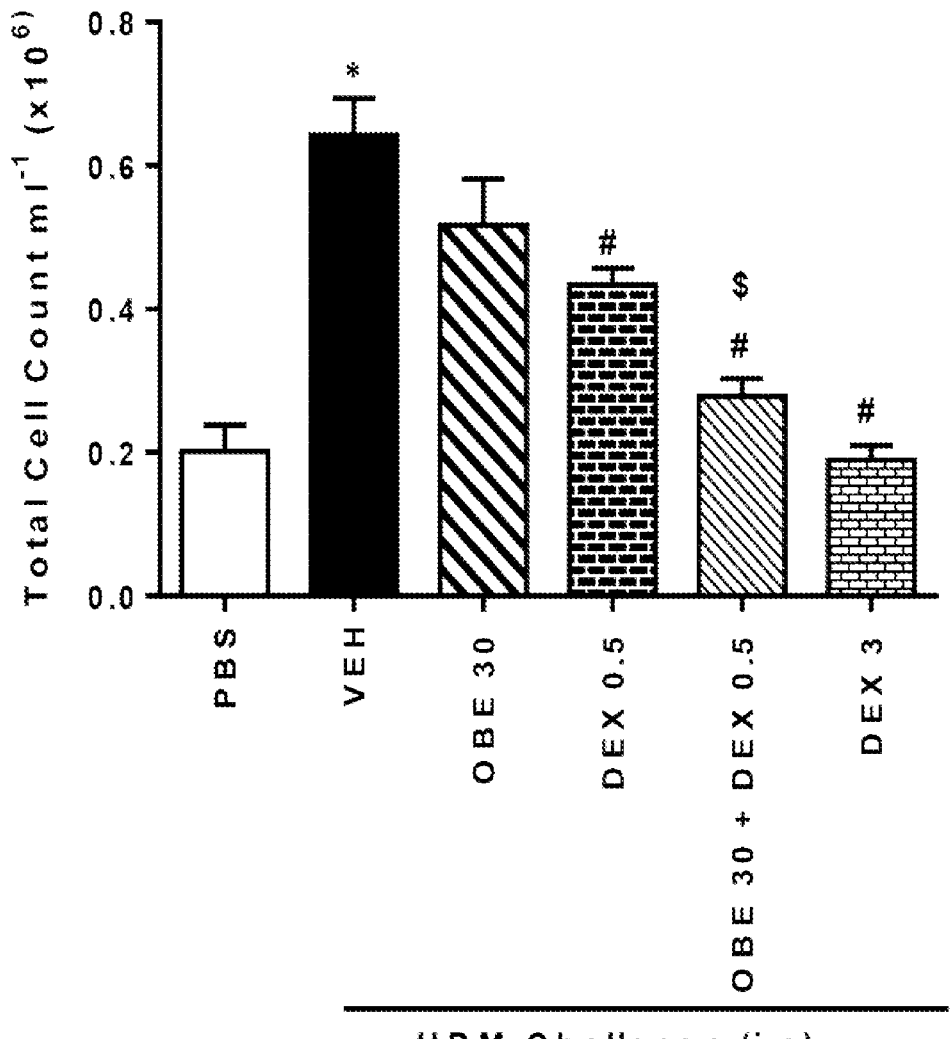
FIG. 1 is a chart comparing the effect of onion bulb extract (OBE) (30 mg/kg; i.p.) both alone and in combination with low dose dexamethasone (0.5 mg/kg) on house dust mite (HDM)-induced total cell influx.

As used herein, the term "glucocorticosteroid" means a corticosteroid that binds to the glucocorticoid receptor and reduces the inflammatory response of the immune system.

Glucocorticosteroids contemplated by the present subject matter include at least cortisol, cortisone, prednisone, prednisolone, methylpredisone, dexamethasone, betamethasone, triamcinolone, fludrocortisone acetate, deoxycorticosterone acetate, aldosterone, and beclometasone.

As used herein, the term "inflammatory disease" includes but is not limited to allergies, asthma, autoimmune diseases, and sepsis.

As used herein, the term "subject" refers to an animal in need of treatment, such as a human being or other mammal. The subject may need treatment to reduce the effects of an inflammatory disease, including but not limited to asthma or allergies.

Steroids, such as glucocorticosteroids, may be administered in "low dose" or standard dose amounts. These dosages vary for the particular steroid, but are characterized by different effects on a subject. Standard dose amounts are generally understood to be required to suppress inflammatory disease related symptoms. By way of example only, a low dose of prednisone might be 2.5 to 10 mg/day, while a high dose might be 1 to 1.5 mg/kg/day (not to exceed 80 to 100 mg/day). Prescribed doses will vary depending upon the specific steroid, the subject, and the specific disease being treated.

As used herein, "low dose dexamethasone" may refer to administration of dexamethsone to a subject in need thereof at a dose that is significantly less than the standard dose. In an embodiment, low dose dexamethasone may include a dose of dexamethosone that is between 50% and 5% of the standard dose. Thus, if the standard dose of dexamethasone is 3 mg/kg, an example low dose is 0.5 mg/kg. In further embodiments, low dose dexamethasone may include any dose that is reduced by at least one-half from the standard dose for the particular disease being treated. Thus, low dose dexamethosone may include 50%, 45%, 40%, 30%, 25%, 20%, 15%, 10%, or 5% of the standard dose, for example.

As used herein, the term "about", when modifying a numerical value, means within 10% of the stated numerical value.

Our work shows that when glucocorticosteroids (GCS) are combined with onion bulb extract (OBE), this combination results in a powerful anti-inflammatory action which is greater than when each component is given alone. Currently GCS are the most effective anti-inflammatory drugs available in the market, but their use is associated with a dose-dependent high side effect profile, particularly when they are used at high doses and for a long time. Our work shows that when steroids are combined with onion bulb extract (OBE), this combination will result in a powerful anti-inflammatory action. In particular, combining low dose steroid (which usually has no or minimal pharmacological action) with OBE resulted in anti-inflammatory effects that were at least equal to the effects seen only with high dose of GCS. This suggests that there is a synergistic effect when OBE is combined with a low dose of steroids, and this results in effective anti-inflammatory action. This combination (OBE and GCS) may, thus, overcome the need to use high doses of steroids and prevent the side effects that are associated with the use of GCS.

Synergism is a phenomenon whereby a combination of drugs produces a greater effect than when each drug is given alone. This phenomenon is useful when low doses of efficacious drugs are combined, as they produce a superior effect, but with fewer side effects. Indeed, this has been demonstrated with ICS and several drug classes, such as LABA and anti-leukotrienes. However, no study has tested whether synergism occurs between steroids and natural products within the context of inflammatory-based diseases, such as asthma.

*Allium cepa* L. (Family Amaryllidaceae) is one of the most commonly consumed vegetables and has also been used for medicinal purposes for numerous ailments, such as ulcer wounds, scars, dysentery, inflammation, hypertension, and also in respiratory conditions, such as cough, asthma and bronchitis. Onion bulb extract (OBE) has also been shown to effectively reduce airway inflammation, IL4 and IgE levels and induce oxidation in animal models of asthma. Thiosulfinates (TS) and cepaenes (CS), isolated from onions and/or synthesized, were also shown to have dose-dependent inhibitory effects on both cyclooxygenase and 5-lipoxygenase activity and inhibit in vitro chemotaxis of human granulocytes induced by formyl-methionine-leucine-phenylalanine (WKYMvm). In this regard, it is of interest to note that many of the previous studies that assessed the effects of onion extract have used ovalbumin as the allergenic material to induce airways inflammation. However, the use of ovalbumin has recently been questioned on the basis that it is not clinically relevant, and therefore studies using allergens (such as house dust mite or *Alternaria alternata*) that simulate clinical asthma more closely are necessary in order to better assess the effects of onion extract in animal models.

The EGFR/ERK1/2/AKT signaling pathway has been recently shown to be an important signaling pathway, in both clinical and preclinical studies. However, whether the EGFR/ERK1/2/AKT signaling pathway is a target for OBE in clinically relevant animal models of allergic asthma is not known. Whether OBE synergizes with steroids to result in dose lowering has not been studied previously. In this study, using a clinically relevant allergen (HDM), we investigated (1) whether the EGFR/ERK1/2/AKT signaling pathway is modulated by OBE; and (2) if OBE synergizes with dexamethasone to result in a greater pharmacological anti-inflammatory action, and thus reduces its side-effect profile.

The anti-inflammatory composition may include a pharmaceutically acceptable carrier. The anti-inflammatory composition may comprise both onion bulb extract and a glucocorticosteroid.

A method of making a pharmaceutical composition may include mixing the anti-inflammatory composition with a pharmaceutically acceptable carrier. For example, the method of making a pharmaceutical composition can include mixing the anti-inflammatory composition extract under sterile conditions with a pharmaceutically acceptable carrier with preservatives, buffers, and/or propellants to create a pharmaceutical composition.

To prepare the pharmaceutical composition, the anti-inflammatory composition, as an active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present composition can be in unit dosage form, such as tablets, pills, capsules, powders, granules, ointments, sterile parenteral solutions or suspensions, metered aerosol or liquid sprays, drops, ampules, auto-injector devices or suppositories, and may be for oral, parenteral, intranasal, sublingual or rectal administration. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical composition may contain, per dosage unit, e.g., tablet, capsule, powder, injection, suppository and the like, an amount of the active ingredient necessary to deliver an effective dose. A therapeutically effective amount of the anti-inflammatory composition, or an amount effective to treat a disease, such as a disease associated with inflammation, may be determined initially from the examples described herein and adjusted for specific targeted diseases using routine methods.

The pharmaceutical composition including the anti-inflammatory composition may be administered to a subject in need thereof. For example, the anti-inflammatory composition can be used to treat a subject suffering from a disease associated with inflammation. The disease can be asthma or other diseases associated with inflammation.

A method of treating an inflammatory disease may comprise administering to a subject in need thereof a therapeutically effective amount of the pharmaceutical composition according to the present subject matter. The inflammatory disease may be asthma.

The anti-inflammatory composition or pharmaceutical compositions thereof can be administered to a subject by any suitable route. For example, the compositions can be administered orally (including bucally and sublingually), nasally, rectally, intracisternally, intravaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body, such as in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

The anti-inflammatory composition may comprise onion bulb extract prepared by percolating fresh onion bulb in dichloromethane and drying the dichloromethane layers to obtain a residue.

The onion bulb used to prepare the onion bulb extract (OBE) may be from a red onion. For example, the onion bulb may be from the plant *Allium cepa.*

The OBE may be prepared by peeling and coarsely cutting fresh onion bulb, which may then be percolated multiple times with dicholoromethane. The dichloromethane layer in the percolate may then be separated from the aqueous layer, dried over anhydrous sodium sulfate, and evaporated in vacuo to produce a brownish syrupy residue. The extraction process may be repeated as necessary to obtain a desired amount of residue.

The anti-inflammatory composition may be further understood in view of the following examples.

Example 1

Extract of Onion Bulb

Fresh red onion bulbs were bought from the local market in Kuwait. The plant was identified as *Allium cepa*, and a voucher specimen, number KOE-010, was deposited at the herbarium of Kuwait University (KTUH), College of Science, Kuwait.

About 20 kg of fresh red onion was peeled, coarsely cut and percolated three times, each using 10 L of dichloromethane. The dichloromethane layer of each percolate was separated from the aqueous layer, dried over anhydrous sodium sulfate, and then evaporated in vacuo until dryness to obtain a brownish, syrupy residue. This extraction process was repeated as needed. The treatment stock solution was prepared using the residue and phosphate-buffered saline (PBS) as a vehicle.

The extraction process was repeated four times to afford 7.5 g (0.038% yield) of brownish, syrupy residue.

Example 2

GC-MS Analysis of Onion Bulb Extract

The dichloromethane extract of onion bulbs (1 µl sample size) was analyzed on a Thermo high resolution gas chromatography-mass spectrometer Double Focusing Sector system (GC-MS DFS) fitted with a DB-5 MS capillary column with 0.25 µm film thickness, 30 m length and 0.25 mm inner diameter, using helium as a carrier gas with a flow rate of 0.8 ml/minute. The operating conditions included the following: a splitless injector with port temperature 250° C., detector temperature 280° C., and program temperature from 50° C. to 250° C. at the rate of 6° C./minute with 10 minutes hold time, and from 250° C. to 300° C. at the rate of 10° C./min with 6 minutes hold time. The MS conditions included the following: electron impact ionization mode, ionization energy 70 eV, ion source temperature 175° C., scan range m/z 40-900 Da. The qualitative identification of the compounds was based on computer matching with NIST MS Search 2.0 library and by comparison with data in the literature.

Dichloromethane extract of *Allium cepa* bulb (OBE) was analyzed to identify different compounds and confirm the identity of the plant. The identified compounds and their mass spectral data are listed in Table 1. The total ion chromatogram (TIC) of the OBE showed 28 different peaks. The major compounds identified in the extract were shown to be the sulfur-containing compounds dipropyl disulfide, dipropyl trisulfide, and propylpropane thiosulfonate. Other sulfur compounds were also identified, but at lesser quantities. The identity of these compounds was confirmed via a direct comparison and matching with the stored spectra in the GC-MS system.

8

TABLE 1

| Compounds Identified in *Allium cepa* Bulb Extract | | |
|---|---|---|
| Identified Compounds | Retention Time $t_r$ (min) | Area (%) |
| Dipropyl disulfide | 8.56 | 45.93 |
| Dipropyl trisulfide | 13.64 | 3.16 |
| 3,5-Diethyl-1,2,4-trithiolane | 13.96 | 1.88 |
| Propylpropane thiosulfonate | 15.09 | 5.07 |
| 1,5-Dithiaspiro[5.6]dodecan-7-ol | 20.32 | 3.46 |
| Methyl-2,6-anhydro-3,4,7-tridesoxy-1-erythrohept-2-enulonate | 22.85 | 1.25 |
| Tricosane | 30.99 | 0.63 |
| Pentacosane | 33.74 | 1.37 |
| 1,2-Benzenedicarboxylic acid | 34.06 | 0.34 |
| Hexacosane | 35.06 | 0.3 |
| 1-Heptacosanol | 35.99 | 0.18 |
| Nonacosane | 36.34 | 1.2 |
| Nonacosane | 39.67 | 1.88 |
| Tetratriacontane | 45.23 | 4.09 |

Example 3

Inhibition of HDM-Induced Asthma Using OBE or a Combination of OBE and Dexamethasone Male BALB/c mice (6-8 weeks old, average weight 25 g) were used in this study. All studies involving animals were in accordance with the ARRIVE guidelines for reporting experiments involving animals. All experimental protocols were approved by the Animal Welfare and Use of Laboratory Animals Committee in the Health Sciences Center, Kuwait University and were carried out in accordance with the EU Directive 2010/63/EU for animal experiments and the National Institutes of Health guide for the care and use of Laboratory animals (NIH Publications No. 8023, revised 1978). Animals were maintained under temperature-controlled conditions with an artificial 12-hour light/dark cycle and were allowed standard chow and water ad libitum.

Seven treatment groups (A-G, 9-15 animals per group) were established to determine whether OBE, if given prophylactically, inhibits the HDM-induced asthma phenotype. All mice were immunized once by intraperitoneal (i.p.) injection of 40 µg HDM in 0.2 ml of alu-Gel-S (Alu-Gel-S; SERVA Electrophoresis GmbH) on day 0. Mice were subsequently challenged on three days (days 14, 17, and 18) with HDM, or with phosphate-buffered saline (PBS) in the case of the control group. Mice in groups A (n=11) and B (n=13) were pretreated intraperitoneally with 0.2 ml of the drug vehicle one hour before each intranasal challenge with PBS or HDM, respectively. In the same manner, groups C (n=10), D (n=9), E (n=10) and F (n=15) were pretreated with the same volume of OBE at 10, 30, 60 and 100 mg/kg, respectively, and group G (n=11) with dexamethasone (3 mg/kg), one hour before each intranasal challenge with HDM.

Twenty-four hours after the last intranasal challenge, half of the animals were sacrificed with an overdose of halothane, bronchoalveolar lavage (BAL) was performed to obtain BAL fluid, and then the lungs were excised in preparation for histology, Western Blot (WB) and immunofluorescence (IF) studies. For the histology/WB/IF studies, the OBE dose of 60 mg/kg was selected to represent the prophylactic approach, as it gave an optimum effect. In the other half of the animals, airway responsiveness was measured.

Six treatment groups (A-F, 9-14 animals per group) were established to determine whether OBE, if given synergistically, inhibits the HDM-induced asthma phenotype. Mice in groups A (n=9) and B (n=11) were pretreated intraperitoneally with 0.2 ml of the drug vehicle one hour before each intranasal challenge with PBS or HDM, respectively. In the same manner, groups C (n=11), D (n=7), E (n=11), and F (n=9) were pretreated with the same volume of OBE at 30 mg/kg (OBE 30), OBE at 30 mg/kg in combination with dexamethasone (DEX) at 0.5 mg/kg (OBE 30+DEX 0.5), 0.5 mg/kg (DEX 0.5 mg), and 3 mg/kg (DEX 3 mg), respectively, one hour before each intranasal challenge with HDM. Treatment with OBE was also repeated on days 14, 17 and 18.

BAL fluid was collected by cannulating the trachea and washing the lungs with saline solution (0.3 ml×4 each) after sacrificing the animals with an over dose of halothane. The BAL cells were then counted using a particle-size counter (Z1 Single Threshold; Beckman Coulter) and cytosmears were prepared for differential count. The cells were stained with Diff-Quik and a differential count of 200 cells was performed using standard morphological criteria. Results are expressed as total cell count/ml and as total macrophages, lymphocytes, neutrophils, and eosinophils/ml in BAL fluid. For histological assessment, segments of lung tissue were removed and fixed in 10% buffered formalin, embedded in paraffin wax, and sectioned into 5-μm-thick slices. The sections were processed and stained separately with H&E stain and periodic acid-Schiff (PAS) according to standard methods as previously described in the literature. Sections were examined under light microscope, and the severity of pathologic changes scored independently by two experienced histologists unfamiliar with the slides. Score coding was as follows: 1=normal, 2=mild, 3=moderate, 4=severe and 5=highly severe.

Airway responsiveness was measured 24 h after the last HDM or PBS challenge, using a separate set of animals using the Buxco FinePointe series RC site (DSI, Wilmington, NC) as described previously in the literature. Briefly, mice were anesthetized with an intraperitoneal injection of ketamine/xylazine (1:0.1 mg/kg) cocktail and tracheotomized with a steel 18-gauge cannula. Mice were then mechanically ventilated at a rate of 150 breaths/minute and a tidal volume of 0.15 ml using a computerized small animal ventilator (FinePointe site). Following a 5 min period of stabilization and administration of PBS, airway resistance was measured by exposing mice to aerosolized methacholine (6.25-50.0 mg/ml, 5 μl per delivery) delivered by an aerogen nebulizer and reported as total lung resistance (RL) (cm $H_2O$ per ml/sec).

Lung tissues were processed as described above. Immunofluorescence was performed as previously described in the literature. In short, lung sections were incubated in a blocking solution (5% bovine serum albumin (BSA)+0.3% Triton X-100 in PBS) for 1 hour, and were subsequently incubated overnight at 4° C. with primary antibodies [p-EGFR (Tyr1068) (Rabbit; Cat. No. 3777S), pAKT (Ser 473) (Rabbit; Cat. No. 9271L) and pERK1/2 (Thr202/Tyr204) (Rabbit; Cat. No. 9101L) (1:25-1:800 dilution) or only 1% BSA (for negative control); Cell Signaling, USA], diluted in 1% blocking solution. Twenty-four hours later, the sections were washed and incubated with secondary antibody conjugated to Alexa Fluor 555 (Goat anti rabbit SFX kit; Life Technologies, USA, 1:400 dilution) for 2 hours at room temperature in the dark. Following several washes in PBS, the sections were stained with 4',6-diamidino-2-phenylindole and mounted. Images were then captured on a ZEISS LSM 700 confocal microscope, and fluorescence intensity was estimated in defined fields using an Image J software package. The laser setting and photo processing were equal among the different treatment groups for each protein. At 40× magnification, the tested molecules were equally modified in terms of sharpness and contrast to show localization of the phospho-proteins in the lung tissue.

For Western blotting, appropriate lobes from the dissected lungs of the mice were snap-frozen in liquid nitrogen and stored at −80° C. Following that, the tissue samples were defrosted in ice then transferred to lysis buffer (pH 7.6) containing 50 mM Tris-base, 5 mM EGTA, 150 mM NaCl, 1% Triton 100, 2 mM $Na_3VO_4$, 50 mM NAF, 1 mM PMSF, 20 μM phenyl arsine, 10 mM sodium molybdate, 10 μg/mL leupeptin and 8 μg/mL aprotinin. Using a homogenizer, the tissues were homogenized for 10 seconds, 3 times. Samples were allowed to lyse completely by incubation on ice for 30 min. The lysates were then centrifuged at 13000 rpm for 10 minutes at 4° C. and the supernatants collected and protein concentrations were estimated by Bio-Rad Bradford Protein Assay (Bio-Rad, Hercules, CA, USA). Aliquots containing equal amounts of protein were subjected to SDS-PAGE and transferred electrophoretically onto nitrocellulose membrane (Schleicher & Schuell, Dassel, Germany). The membranes were blocked with 5% BSA and then incubated with ERK1/2 (137F5) (Rabbit; Cat. No. 4695S), pERK1/2 (Thr202/Tyr204) (Rabbit; Cat. No. 9101L) and β-actin antibody (Cell Signaling Technology, Boston, MA, USA; 1/1000 dilution) (used as loading control, 1:1000 in 5% BSA) at 4° C. overnight. Membranes were incubated with appropriate secondary antibodies conjugated to horseradish peroxidase (Amersham, Buckinghamshire, UK) to detect phosphorylated form of ERK1/2 (42/44 kDa), or total form of actin (45 kDa). The immunoreactive bands were detected with Super Signal Chemiluminescent Substrate (Immuno Cruz Western blotting luminal reagent SC-20428, Santa Cruz Biotechnology) utilizing a Kodak autoradiography film (Care stream Biomax Xarfil 1660760). Images were then analyzed and quantified, and the data were normalized to β-actin levels. The experiment was run twice with lung samples from three different mice in each treatment group (pooled).

Lung tissues from mice in the prophylactic study were collected and stored at −80° C. The amount of total protein was determined by Bradford analysis using the Bio-Rad Protein Assay reagent. The relative changes of different cytokines and chemokines were detected using Proteome Profiler™ Mouse Cytokine Array Kit (Catalog #ARY006, R&D Systems, Inc., Minneapolis, USA). The procedure was done in line with the manufacturer's protocols and as recently described in the literature.

To isolate human blood eosinophils, fresh blood was obtained from healthy individuals with no history of allergic disease and who had not taken any medication in the last 72 hours, after receiving their informed consent. The methods and protocol for these experiments were performed in accordance with and approved by the "Ethical Committee of the Faculty of Medicine, Kuwait University". Granulocytes were isolated from heparinized (10 IU/ml) blood by erythrocyte sedimentation, followed by percoll gradient centrifugation as reported recently in the literature. Eosinophils were separated using negative selection with the immunomagnetic method as previously described in the literature. The eosinophil purity was checked by differential count of a Wright-Giemsa stained cytosmear and was routinely >98%. Viability was determined by Trypan blue exclusion and exceeded 98%.

These peripheral blood-derived eosinophils were used for a chemotaxis assay utilizing a Boyden chamber as previously described in the literature. Purified naïve eosinophils $(2\times10^5)$ were then placed in the upper wells, and 500 μl of BAL fluid derived from mice challenged with PBS (vehicle) or with HDM and pretreated ex vivo with either vehicle or OBE (100 and 1000 ng/ml) was placed in the lower wells (37° C./5% $CO_2$), and eosinophils were allowed to migrate for 1 hour. The transmigrated eosinophils were determined by counting under the microscope by using a hemocytometer.

All numerical values were expressed as means±SEM. Total cell counts represent the number of cells/ml of BAL fluid. Differential cell counts represent the absolute number of each cell type/ml of BAL fluid. Absolute $R_L$ values were computed and were used as an index of airway responsiveness. For the histopathological assessment, a semi-quantitative 5-level lung pathology score was used to grade the degree of inflammation in each microscopic field at 20×. All data were initially assessed for normality. One-way analysis of variance (ANOVA) test followed by Bonferroni post hoc was used to compare differences between individual groups for both total and differential cell count, as well as his-topathological data and the immunofluorescence data for both the prophylactic and the synergistic studies. A two-way repeated measure analysis of variance followed by a Bon-ferroni post hoc test was used for the airway responsiveness data. The mean difference was considered as significant at a probability level of less than 0.05. All analyses were performed using GraphPad Prism.

Figure 2:
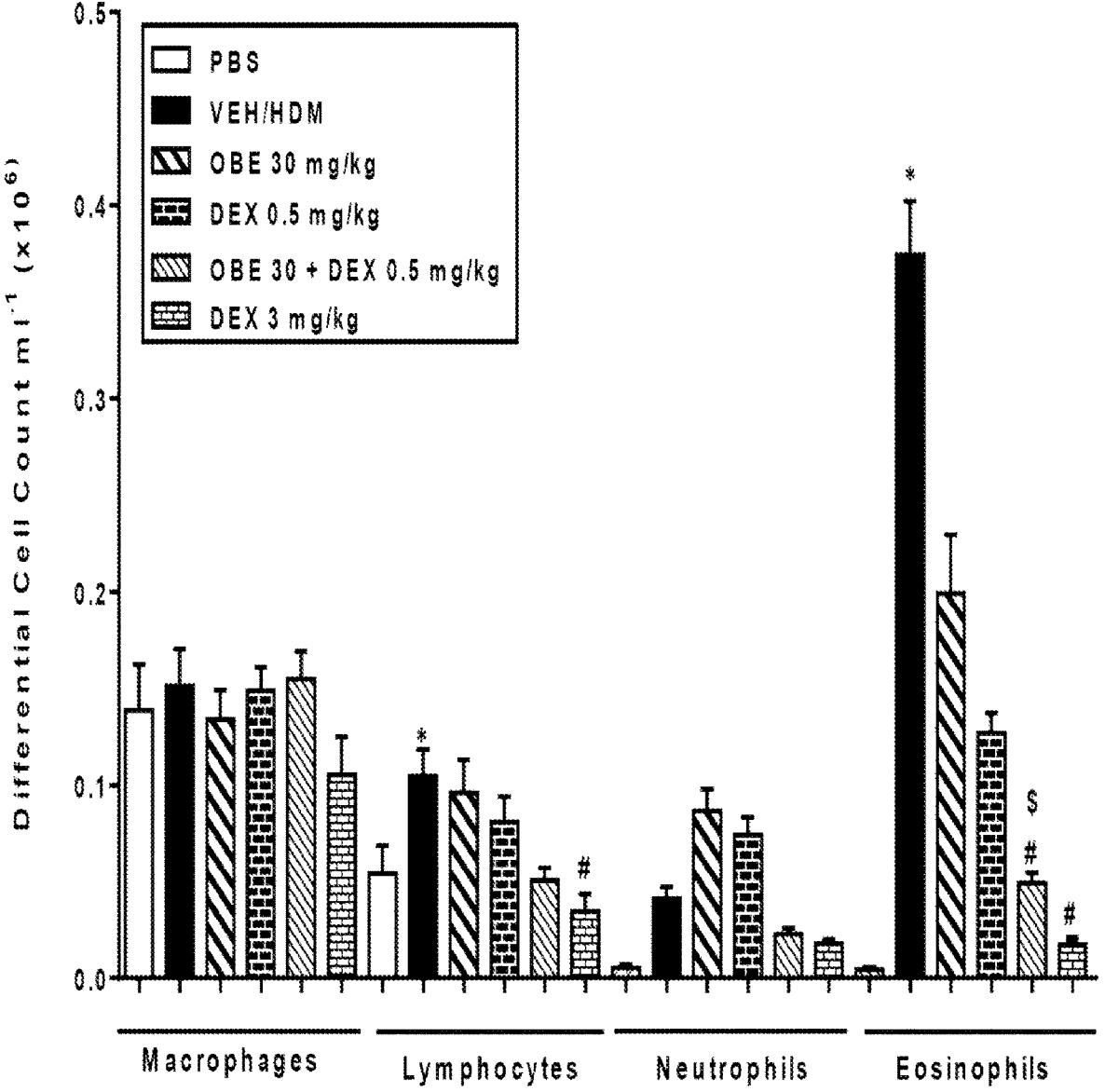
FIG. 2 is a chart comparing the effect of onion bulb extract (OBE) (30 mg/kg; i.p.) both alone and in combination with low dose dexamethasone (0.5 mg/kg) on HDM-induced differential cell influx.
Figures 3A, 3B, 3C, 3D, 3E, 3F:
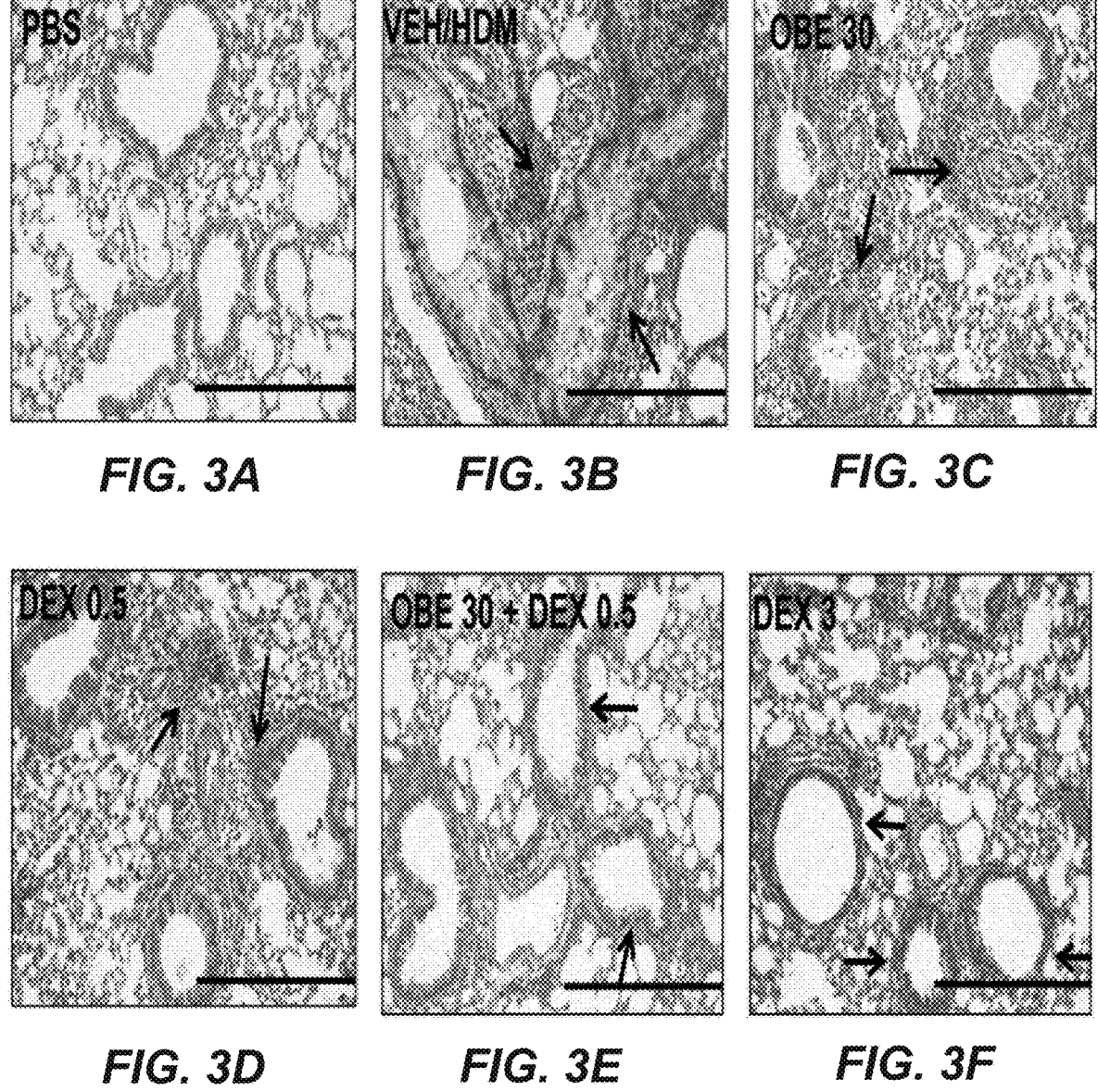
FIG. 3A is a photomicrograph of a whole lung tissue sample from a control phosphate-buffered saline (PBS)-challenged mouse (PBS).
FIG. 3B is a photomicrograph of a whole lung tissue sample from an HDM-challenged mouse (VEH/HDM).
FIG. 3C is a photomicrograph of a whole lung tissue sample from an HDM-challenged mouse pretreated with OBE (30 mg/kg; i.p.) (OBE 30).
FIG. 3D is a photomicrograph of a whole lung tissue sample from an HDM-challenged mouse pretreated with low dose dexamethasone (0.5 mg/kg; i.p.) (DEX 0.5).
FIG. 3E is a photomicrograph of a whole lung tissue sample from an HDM-challenged mouse pretreated with a combination of OBE (30 mg/kg; i.p.) and low dose dexamethasone (0.5 mg/kg i.p.) (OBE 30+DEX 0.5).
FIG. 3F is a photomicrograph of a whole lung tissue sample from an HDM-challenged mouse pretreated with high dose dexamethasone (3 mg/kg; i.p.) (DEX 3).

In these experiments, we evaluated the effect of OBE on HDM-induced total and differential cell influx. We found that HDM-sensitized and challenged animals (HDM group) developed a significant increase in total cell count (1.3±0.3 vs 11.0±2.0×$10^5$ cells/ml), as well as in lymphocytes (0.03±0.01 vs 1.9±0.6×105 cells/ml) and eosinophils (0.04±0.02 vs 4.9±0.6×105 cells/ml), (P<0.05; n=9-15), 24 hours after the last HDM challenge compared to the control group. Prophylactic treatment with OBE (10, 30, 60 and 100 mg/kg) dose-dependently inhibited the HDM-induced increase in the total cells and was significant at the doses of 60 and 100 mg/kg (3.3±0.7 and 2.2±0.4 vs 11.0±2.0×105, respectively, P<0.05; n=9-15) and were comparable to the dexamethasone (DEX) group (used as a positive control). Moreover, OBE treatment also inhibited the HDM-induced increase in lymphocytes (0.4±0.2 vs 1.9±0.6×105 cells/ml, P<0.05; FIG. 2, n=9-15) and eosinophils (0.6±0.2 vs 4.9±0.6×105 cells/ml, P<0.05; n=9-15).

H&E and PAS stained lung sections from control mice (PBS group) showed normal histology. In contrast, lung sections from mice challenged with HDM showed consistently marked and severe perivascular and peribronchial inflammatory cell infiltration (cellular infiltration score, HDM vs PBS, 4.2±0.2 vs 1.0±0.07) and increase in bronchial mucus production and goblet cell hyper/metaplasia (mucous intensity score, HDM vs PBS, 4.1±0.3 vs 1.0±0.02) demonstrating a marked degree in airway remodeling (P<0.05; n=3-6). However, lung sections from OBE-treated mice (60 mg/kg) showed significantly low score of the histopathological parameters that were assessed (cellular infiltration score; 2.7±0.3 vs 4.2±0.2, and mucous intensity score; 2.3±0.5 vs 4.1±0.3) respectively, achieving almost normal histological appearance that was very similar to the dexamethasone treatment group (P<0.05; n=3-6).

Our findings show that HDM challenge induced a significant increase of about 3.0-, 2.3-, and 2.4-fold in the phosphorylation of EGFR, ERK1/2 and AKT, respectively, compared to PBS control, as detected by immunofluorescence (P<0.05; n=3-5). A negative control showed no nonspecific staining. Treatment with OBE (60 mg/kg) significantly inhibited the HDM-induced phosphorylation of all proteins (P<0.05) and was comparable to the inhibition obtained in the dexamethasone treatment group (P<0.05, n=3-5).

An assessment of the levels of p-ERK1/2 and total ERK1/2 was conducted by Western blotting in order to confirm and validate the immunofluorescence data. Western blotting analysis of lung homogenate confirmed the modulated levels of p-ERK1/2 seen in the immunofluorescence study. HDM challenge resulted in a marked increase in p-ERK1/2 levels compared to PBS-challenged mice. Treatment with OBE resulted in a clear inhibition of the p-ERK1/2 and was similar to the dexamethasone-treated group (n=3 for each blot). The effect of HDM and OBE on total ERK1/2 was relatively unchanged.

The effect of OBE treatment (60 mg/kg) on the airway expression levels of various pro-inflammatory cytokines was determined. HDM challenge significantly enhanced the expression of the following interleukins (IL): IL-3 (147.4%), IL-4 (104.6%), IL-5 (5400%), IL-10 (152.0%), and tumor necrosis factor (TNF-α) (17200%) (P<0.05; n=4), compared to PBS challenged mice. Treatment with OBE significantly reduced the expression of all of the above molecules by approximately 98.2%-99.5%, except IL-10 (anti-inflammatory cytokine), which was significantly increased (78.6%) above the HDM levels (P<0.05; n=4).

In experiments conducted to determine the effect of OBE on eosinophil chemotaxis ex vivo, eosinophils showed significant migration towards BAL fluid derived from HDM-challenged mice compared to BAL fluid from PBS-challenged mice (16.5±2.4 vs 4.2±0.6×$10^4$/ml, P<0.05). In contrast, pretreatment with OBE (100 and 1000 ng/ml) dose-dependently inhibited the HDM/BAL fluid-induced eosinophil chemotaxis (6.4±1.0 and 3.7±0.5 vs 16.5±2.4× $10^4$/ml, respectively, P<0.05; n=5).

In experiments designed to measure the effect of OBE on HDM-induced airway hyperresponsiveness (AHR), we evaluated the effect of OBE treatment on the HDM-induced AHR (n=6-13). Our data show that there was a significant increase in airway responsiveness 24 h after the last intra-nasal HDM challenge, as demonstrated by a significant increase in lung resistance ($R_L$) to methacholine in the HDM-challenged mice as compared to the PBS-treated control mice at a dose of 25 mg/ml (5.2±0.2 vs 3.9±0.2 cm $H_2O$ per ml/sec) and 50 mg/ml (7.9±0.5 vs 4.6±0.3 cm $H_2O$ per ml/sec) (P<0.05). However, treatment with OBE did not significantly reduce the average $R_L$ in comparison with the HDM-challenged/vehicle-treated group at any of the tested doses of methacholine (P>0.05). Treatment with dexamethasone (3 mg/kg) resulted in a significant reduction (7.9±0.5 vs 5.2±0.8 cm $H_2O$ per ml/sec) (P<0.05) of the HDM-induced AHR at 50 mg/ml of methacholine.

In experiments designed to measure the synergy between OBE and dexamethasone on airway inflammatory cell influx, we evaluated the effect of combining OBE with dexamethasone on the HDM-induced total and differential cell influx. Treatment with either OBE 30 mg/kg or 0.5 mg/kg of dexamethasone had minimal non-significant effect on the HDM-induced increase in the total cell count (5.2±0.6 and 4.3±0.2 vs 6.4±0.5×$10^5$, respectively, P>0.05; n=7-11) (See FIG. 1). Treatment with OBE, in combination with low dose dexamethasone, resulted in a significant inhibition of total cell numbers, compared to treatment with either alone. In FIG. 1, data are expressed as mean±SEM (n=7-11), *P<0.05 vs PBS group, #P<0.05 vs HDM group and $P<0.05 versus either OBE (30 mg/kg; i.p.) alone or dexamethasone (0.5 mg/kg/i.p.) alone. Furthermore, while treatment with either OBE at 30 mg/kg or dexamethasone at 0.5 mg/kg, alone reduced the eosinophil influx, this did not reach statistical significance (OBE 30 and 0.5 dexamethasone alone vs HDM, $1.9\pm0.3$ and $1.3\pm0.1$ vs $3.7\pm0.3\times10^5$, respectively, P>0.05) (See FIG. 2). Treatment with OBE, in combination with low dose dexamethasone, resulted in a significant inhibition of eosinophil numbers compared to treatment with either alone. In FIG. 2, data are expressed as mean±SEM (n=7-11), *P<0.05 vs PBS group, #P<0.05 vs HDM group and $P<0.05 versus either OBE (30 mg/kg; i.p.) alone or dexamethasone (0.5 mg/kg; i.p.) alone. However, when OBE at 30 mg/kg was combined with 0.5 mg/kg dexamethasone, the inhibitory effect of this combination was significantly greater than either OBE (30 mg/kg) or dexamethasone (0.5 mg/kg) given alone on HDM-induced total influx ($2.7\pm0.2$ vs $5.2\pm0.6$, $4.3\pm0.2$, $6.4\pm0.5\times10^5$, respectively, P<0.05) and was indeed comparable to the high dose dexamethasone (3 mg/kg). Similarly, the combined treatment of both OBE (30 mg/kg) and dexamethasone (0.5 mg/kg), compared to when either OBE (30 mg/kg) or dexamethasone (0.5 mg/kg) were given alone resulted in a significant reduction in the HDM-induced airways eosinophilia ($0.4\pm0.1$ vs $1.9\pm0.3$, $1.3\pm0.1$, $3.7\pm0.3\times10^5$, respectively, P<0.05) and was comparable to the high dose dexamethasone treatment (3 mg/kg) (See FIG. 2).

Figure 4:
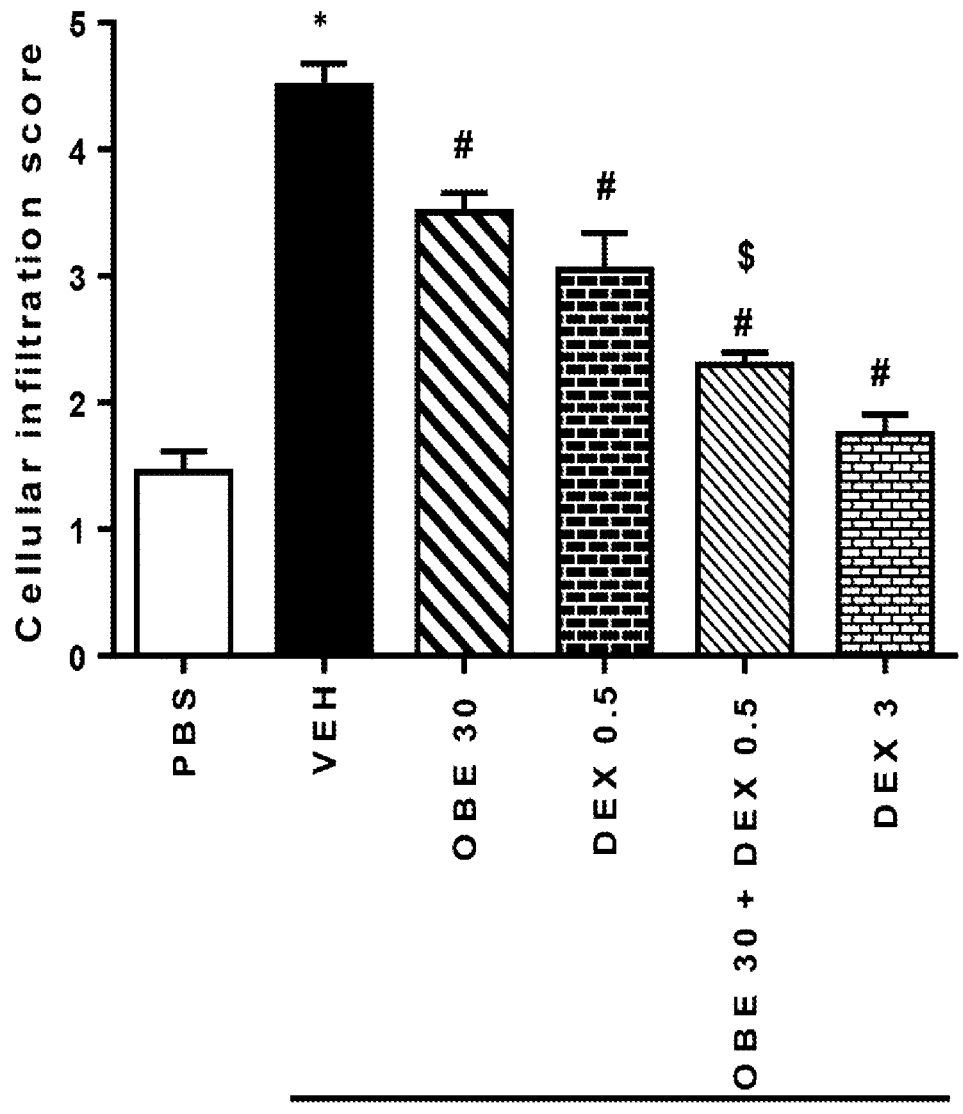
FIG. 4 is a chart comparing the cellular infiltration score for OBE (30 mg/kg i.p.) alone and in combination with low dexamethasone (0.5 mg/kg) on HDM-induced peribronchial and perivascular inflammatory cell infiltration.

Our data also show that treatment with either OBE (30 mg/kg) or dexamethasone (0.5 mg/kg) alone resulted in modest but significant reduction in HDM-induced perivascular and peribronchial inflammation (cellular infiltration score; $3.5\pm0.2$ and $3.1\pm0.3$ vs $4.5\pm0.2$, respectively, P<0.05; n=5), (See FIGS. 3A-3F and FIG. 4). OBE treatment in combination with low dose dexamethasone resulted in a significant decrease in both peribronchial and perivascular inflammatory cell infiltration compared to either treatment when given alone. In FIG. 4, data are expressed as mean±SEM (n=5), *P<0.05 vs PBS, #P<0.05 vs HDM and $P<0.05 vs either the OBE (30 mg/kg i.p.) alone group or the low dose dexamethasone (0.5 mg/kg i.p.) alone group. However, when OBE (30 mg/kg) was combined with dexamethasone (0.5 mg/kg), the inhibitory effect on HDM-induced perivascular and peribronchial inflammation was now more marked and significantly greater than each treatment given alone (cellular infiltration score, $2.3\pm0.1$ vs $3.5\pm0.2$, $3.1\pm0.3$, $4.5\pm0.2$, respectively, P<0.05) and was similar to the high dose dexamethasone (3 mg/kg) treatment. Similarly, treatment with either OBE (30 mg/kg) or dexamethasone (0.5 mg/kg) alone resulted in a modest reduction in the HDM-induced goblet cell hyper/metaplasia and increase in bronchial mucus production (mucous intensity score; $3.5\pm0.2$ and $3.0\pm0.2$ vs $4.2\pm0.2$, respectively, P<0.05; n=5). However, the combination treatment of OBE (30 mg/kg) with dexamethasone (0.5 mg) significantly inhibited the goblet cell hyper/metaplasia and increase in bronchial mucus production when compared to either OBE (30 mg/kg) or dexamethasone (0.5 mg/kg) given alone (mucous intensity score; $2.2\pm0.4$ vs $3.5\pm0.2$, $3.0\pm0.2$, $4.2\pm0.2$, respectively, P<0.05) and was almost as effective as dexamethasone at 3 mg/kg.

Further data showed that treatment with either only OBE (30 mg/kg) or only low dose dexamethasone (0.5 mg/kg) did not result in marked inhibition of the HDM-induced phosphorylation of ERK1/2 ($267.0\pm13.8$ and $264.8\pm4.9$ vs $319.0\pm10.4\%$, respectively, P<0.05; n=4-5). However, when OBE (30 mg/kg) was combined with the low dose dexamethasone (0.5 mg/kg), there was now a marked and significant reduction in pERK1/2 levels compared to either OBE (30 mg/kg) or the low dose dexamethasone (0.5 mg/kg) alone ($80.0\pm16.0$ vs $267.0\pm13.8$ and $264.8\pm4.9$, respectively, P<0.05). Of interest, the inhibitory effect on pERK1/2 in the combination treatment was 2.0-fold greater than what was obtained with the high dexamethasone dose (3 mg/kg) (P<0.05).

We found that combined treatment with OBE and a classical steroid (dexamethasone) at sub-maximal doses resulted in an enhanced anti-inflammatory effect at the cellular, histopathological and molecular levels.

Our data show that OBE dose-dependently decreased the total and differential cell influx into the airways, at both 60 and 100 mg/kg dose, confirming data from recent studies reporting its inhibitory effect on BAL fluid cellularity. In line with this, we found that a 60 mg/kg dose of OBE resulted in significant reduction of the HDM-induced perivascular and peribronchial inflammatory cell infiltration and goblet cell hyper/metaplasia.

These anti-inflammatory actions were comparable to the action of dexamethasone (3 mg/kg), which indicates that the anti-inflammatory action of OBE is at least as effective as that of steroids. This study also suggests that since dichloromethane was used for extraction, the observed anti-inflammatory action is most likely due to nonpolar, fat-soluble constituents, such as sulfur-containing compounds, mainly dipropyl disulfide and dipropyl trisulfide, which are found in abundance in the essential oil of onion.

EGF/EGFR is a critical signaling pathway in the pathogenesis of asthma, and both EGF and EGFR levels have been shown to be consistently increased in both human asthma and in animal models of asthma. However, other ligands, such as heparin-binding EGF-like growth factor (HB-EGF), amphiregulin and betacellulin can also bind to and activate EGFR. In addition, ERK1/2 and AKT are not only key signaling molecules in asthma, but have also been recently shown to be downstream of EGFR activation. Our data show that treatment with OBE not only inhibited the development of asthma, but also reduced pEGFR levels. Of interest and relevance, data from a recent study from our group, and that of others, using a similar model of asthma, has shown that treatment with selective EGFR inhibitors inhibited the EGFR-dependent signaling pathway and also reduced eosinophil recruitment, airway inflammation, AHR and goblet cell hyper/metaplasia. Therefore, our findings would imply that the inhibitory effects of OBE on the asthmatic phenotype may be at least partly via inhibition of EGFR-dependent signaling perturbation. However, it is also likely that in addition to the EGFR pathway, OBE may inhibit other pro-inflammatory signaling pathways.

Our data also show that an HDM-induced increase in pERK1/2 and pAKT were both inhibited following OBE treatment. While it is plausible that the effect of OBE on these signaling molecules represents independent and separate effects, since both pERK1/2 and pAKT are ubiquitous signaling molecules, we have previously reported that AG1478, a selective EGFR receptor inhibitor, inhibited not only EGFR activation, but also decreased pERK1/2 and pAKT levels, suggesting that both molecules are downstream of EGFR activation. Therefore, it is very likely that the inhibitory effect of OBE on these two molecules is primarily due to upstream inhibition of EGFR-dependent signaling. This notion is further confirmed by our recent study showing that the effects of the anti-inflammatory endogenous molecule Ang-(1-7) in asthma are mediated via inhibition of the EGFR/ERK1/2 dependent signaling. That OBE can inhibit the EGFR-triggered signaling perturbations suggests that it can inhibit a central signaling pathway in asthma.

It is well recognized that asthma is an immune response driven by Th2 and Th17 cells, with cytokines, such as IL-4, IL-5, IL-9, IL-10, IL-13, and IL-7, playing important roles. Moreover, Th1 cytokines, such as TNF-$\alpha$ and IFN-$\alpha$, are also involved in asthma, with pro- and anti-asthma effects, respectively. Our findings show that OBE treatment resulted in a significant reduction of IL-4 and IL-5, consistent with other studies and the effects of drugs that mediate an anti-allergic/anti-asthma action. In addition, OBE treatment decreased the pro-asthma TNF-$\alpha$ cytokine, but increased the Th2 anti-inflammatory cytokine, IL-10. It is therefore plausible that the OBE-induced increase in IL-10 levels may, in part, explain the anti-inflammatory action of OBE in general and/or the specific decrease in the levels of IL-4 and IL-5, as these cytokines are known to have a reciprocal relationship.

The recent introduction of monoclonal antibodies targeting the eosinophil chemoattractant underscores the importance of eosinophils in asthma. Our data show that treatment with OBE significantly reduced eosinophil numbers, not only in the tissue, but also their ex vivo chemotaxis towards BAL fluid from HDM-challenged mice. Studies have shown that onion constituents, such as thiosulfinates and cepaenes, dose-dependently inhibit both cyclooxygenase and 5-lipoxygenase enzyme activity. Furthermore, products of 5-lipoxygenase, namely, the cysteinyl leukotrienes LTC4, LTD4, and LTE4, are known to be potent inducers of eosinophil chemotaxis. Therefore, inhibition of 5-lipoxygenase may represent one possible mechanism by which OBE inhibits eosinophil chemotaxis.

Our data also show that HDM challenge resulted in an enhancement of the AHR, a characteristic feature of both clinical and preclinical asthma that is not easily amenable to asthma therapy. Unfortunately, treatment with OBE also had no effect on this parameter. Although many studies have reported a causal link between airway inflammation and AHR, others have not been able to confirm this relationship, at least not for all types of AHR. Indeed, there may be a separation between the two phenomena, as not all agents that inhibit airway inflammation reduce AHR and vice versa. Recent studies have also provided good evidence that airway sensory hyper-excitability may also underlie AHR, and hyperactivity of airway nerves is less susceptible to anti-inflammatory agents.

Although ICS have been the mainstay treatment for asthma, being effective anti-inflammatory agents, their major limitation is their high side-effect profile, particularly with moderate-to-high doses. In addition, the high cost of ICS is a real problem in poorer regions of the world. To test whether OBE and a steroid have a synergistic effect, we combined a low dose of OBE, 30 mg/kg, and a low dose of dexamethasone, 0.5 mg/kg, both of which produced minimal to mild anti-inflammatory effect when given alone. An important and novel finding in this study, and to the best of our knowledge the first, is that when OBE is combined with a low dose of dexamethasone, a more powerful and effective anti-inflammatory effect was produced. Our data also show that the combination treatment resulted in a marked and significant enhancement of the anti-inflammatory effects on the total cell, eosinophil influx, histopathological changes (both perivascular and peribronchial inflammation and goblet cell hyper/metaplasia) when compared to either treatment alone. This combination was at least as effective as the high dose (3 mg/kg) steroid. To determine whether this was being mediated via enhanced suppression of the EGFR/ERK1/2/AKT signaling pathway, we assessed p-ERK1/2 expression level as a marker of activation of this signaling pathway. Our results findings clearly show that while neither 0.5 mg/kg dexamethasone nor 30 mg/kg OBE alone had any effect on p-ERK1/2 levels, when both agents are combined, a significant and dramatic decrease in p-ERK1/2 levels was detected. This clearly indicates that the enhanced suppressive effects are being mediated via synergistic actions effected at the molecular level.

In conclusion, our data clearly show that OBE inhibits the asthma phenotype in a clinically relevant murine model of asthma, at least in part via inhibition of the Th2 cytokine profile and via inhibition of the EGFR/ERK/1/2/AKT signaling pathway. In addition, our data also show that combining OBE with steroids resulted in an enhanced anti-inflammatory effect via a synergistic action at the molecular signaling pathway level. Therefore, this study not only identifies an important molecular signaling pathway that is targeted by OBE to inhibit the asthma phenotype, but also shows that OBE synergizes with steroids, resulting in a greater anti-inflammatory action. This finding may have important implications for the treatment of asthma, as it provides a potential to reduce steroid toxicity while maintaining efficacy.

It is to be understood that the anti-inflammatory composition and method of treatment is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of reducing inflammation in an asthmatic patient, comprising the step of administering an anti-inflammatory composition including 30 mg/kg onion bulb (OBE) and 0.5 mg/kg dexamethasone in a single composition to the patient, wherein the anti-inflammatory composition is a single composition which is administered to the patient to achieve a synergistic effect from said single composition such that a reduced dosage amount of the dexamethasone is more effective as an anti-inflammatory treatment for the patient as compared to a dosage amount of the dexamethasone when administered alone.

2. The method of reducing inflammation according to claim 1, wherein the onion bulb extract comprises red onion bulb extracted in an organic solvent.

3. The method of reducing inflammation according to claim 1, wherein the onion blub extract comprises an extract of Allium cepa.

4. A method of treating asthma, comprising the step of administering an anti-inflammatory composition including 30 mg/kg onion bulb (OBE) and 0.5 mg/kg dexamethasone in a single composition to a subject, wherein the anti-inflammatory composition is a single composition which is administered to the subject to achieve a synergistic effect from said single composition such that a reduced dosage amount of the dexamethasone is more effective as an anti-inflammatory treatment for the subject as compared to a dosage amount of the dexamethasone when administered alone.

* * * * *